(12) United States Patent
Germain et al.

(10) Patent No.: US 11,504,181 B2
(45) Date of Patent: Nov. 22, 2022

(54) ARTHROSCOPIC DEVICES AND METHODS

(71) Applicant: RELIGN Corporation, Campbell, CA (US)

(72) Inventors: Aaron Germain, San Jose, CA (US); Jeff Norton, Emerald Hills, CA (US)

(73) Assignee: Relign Corporation, Campbell, CA (US)

( * ) Notice: Subject to any disclaimer, the term of this patent is extended or adjusted under 35 U.S.C. 154(b) by 247 days.

(21) Appl. No.: 16/915,848

(22) Filed: Jun. 29, 2020

(65) Prior Publication Data
US 2021/0000532 A1 Jan. 7, 2021

Related U.S. Application Data

(60) Provisional application No. 62/869,472, filed on Jul. 1, 2019.

(51) Int. Cl.
| | | |
|---|---|---|
| *A61B 18/14* | (2006.01) | |
| *A61B 17/16* | (2006.01) | |
| *A61B 18/16* | (2006.01) | |
| *A61B 17/32* | (2006.01) | |
| *A61B 17/00* | (2006.01) | |

(Continued)

(52) U.S. Cl.
CPC ........ *A61B 18/148* (2013.01); *A61B 17/1615* (2013.01); *A61B 17/32002* (2013.01);
(Continued)

(58) Field of Classification Search
CPC . A61B 17/16; A61B 17/1615; A61B 17/1617; A61B 17/32; A61B 17/32002; A61B 17/1628; A61B 17/1633; A61B 17/1666; A61B 17/1668; A61B 17/00477; A61B 18/148; A61B 18/14; A61B 18/16; A61B 18/1482; A61B 18/1206; A61B 18/1485; A61B 2018/005; A61B 2018/00577; A61B 2018/007;
(Continued)

(56) References Cited

U.S. PATENT DOCUMENTS

| | | | |
|---|---|---|---|
| 5,364,395 A | 11/1994 | West, Jr. | |
| 5,904,681 A | 5/1999 | West, Jr. | |

(Continued)

*Primary Examiner* — Scott A Smith
(74) *Attorney, Agent, or Firm* — Schwegman Lundberg & Woessner, P.A.

(57) ABSTRACT

An arthroscopic system includes a hand piece with a motor drive. an elongate shaft assembly is detachably secured to a distal end of the hand piece, and the elongate shaft assembly includes an outer sleeve and an inner sleeve rotatably mounted in the outer sleeve. The inner sleeve couples to the motor drive when the elongate shaft assembly is attached to the hand piece, and an inner distal cutting window on the inner sleeve moves in and out of alignment with an outer distal cutting window on the outer sleeve as the motor drive rotates the inner sleeve. A distal electrode is disposed on an outer surface of the outer sleeve at a location opposite to that of the outer distal cutting window, and the outer sleeve member is rotatable relative to the hand piece when the hub is secured to the hand piece such that a user can hold the hand piece in one hand and rotate the outer sleeve to selectively place the outer distal cutting window or the distal electrode in an upward orientation relative to the user while continuing to hold the hand piece in the one hand.

25 Claims, 14 Drawing Sheets

(51) Int. Cl.
*A61B 18/00* (2006.01)
*A61B 18/18* (2006.01)

(52) U.S. Cl.
CPC .............. *A61B 18/14* (2013.01); *A61B 18/16* (2013.01); *A61B 18/1482* (2013.01); *A61B 2017/00039* (2013.01); *A61B 2017/0088* (2013.01); *A61B 2017/00424* (2013.01); *A61B 2017/00473* (2013.01); *A61B 2018/00077* (2013.01); *A61B 2018/00184* (2013.01); *A61B 2018/00577* (2013.01); *A61B 2018/00589* (2013.01); *A61B 2018/1861* (2013.01)

(58) Field of Classification Search
CPC .. A61B 2018/00208; A61B 2018/1861; A61B 2217/005; A61B 2217/007
USPC .. 606/32, 41, 45, 46, 48, 50, 170, 171, 177; 604/22, 114
See application file for complete search history.

(56) References Cited

U.S. PATENT DOCUMENTS

| | | | |
|---|---|---|---|
| 6,610,059 B1 | 8/2003 | West, Jr. | |
| 7,674,263 B2 * | 3/2010 | Ryan | A61B 18/148 606/50 |
| 7,699,846 B2 | 4/2010 | Ryan | |
| 8,702,702 B1 * | 4/2014 | Edwards | A61B 17/32002 606/50 |
| 9,681,913 B2 * | 6/2017 | Orczy-Timko | A61B 18/1206 |
| 9,855,675 B1 | 1/2018 | Germain et al. | |
| 10,052,149 B2 | 8/2018 | Germain et al. | |
| 10,327,842 B2 * | 6/2019 | Germain | A61B 17/1628 |
| 10,568,685 B2 * | 2/2020 | Germain | A61B 17/1633 |
| 10,595,889 B2 | 3/2020 | Germain et al. | |
| 2008/0103439 A1 * | 5/2008 | Torrance | A61M 25/09 604/93.01 |
| 2008/0188848 A1 * | 8/2008 | Deutmeyer | A61B 18/1485 606/45 |
| 2013/0296847 A1 * | 11/2013 | Germain | A61B 17/42 606/39 |
| 2016/0346036 A1 * | 12/2016 | Orczy-Timko | A61B 18/14 |
| 2017/0252099 A1 | 9/2017 | Orczy-Timko et al. | |
| 2017/0258519 A1 | 9/2017 | Germain et al. | |
| 2018/0263649 A1 | 9/2018 | Germain et al. | |
| 2018/0303509 A1 | 10/2018 | Germain et al. | |
| 2019/0008538 A1 | 1/2019 | Germain et al. | |
| 2019/0321063 A1 | 10/2019 | Germain et al. | |
| 2019/0321095 A1 | 10/2019 | Germain et al. | |
| 2019/0328417 A1 | 10/2019 | Germain | |

* cited by examiner

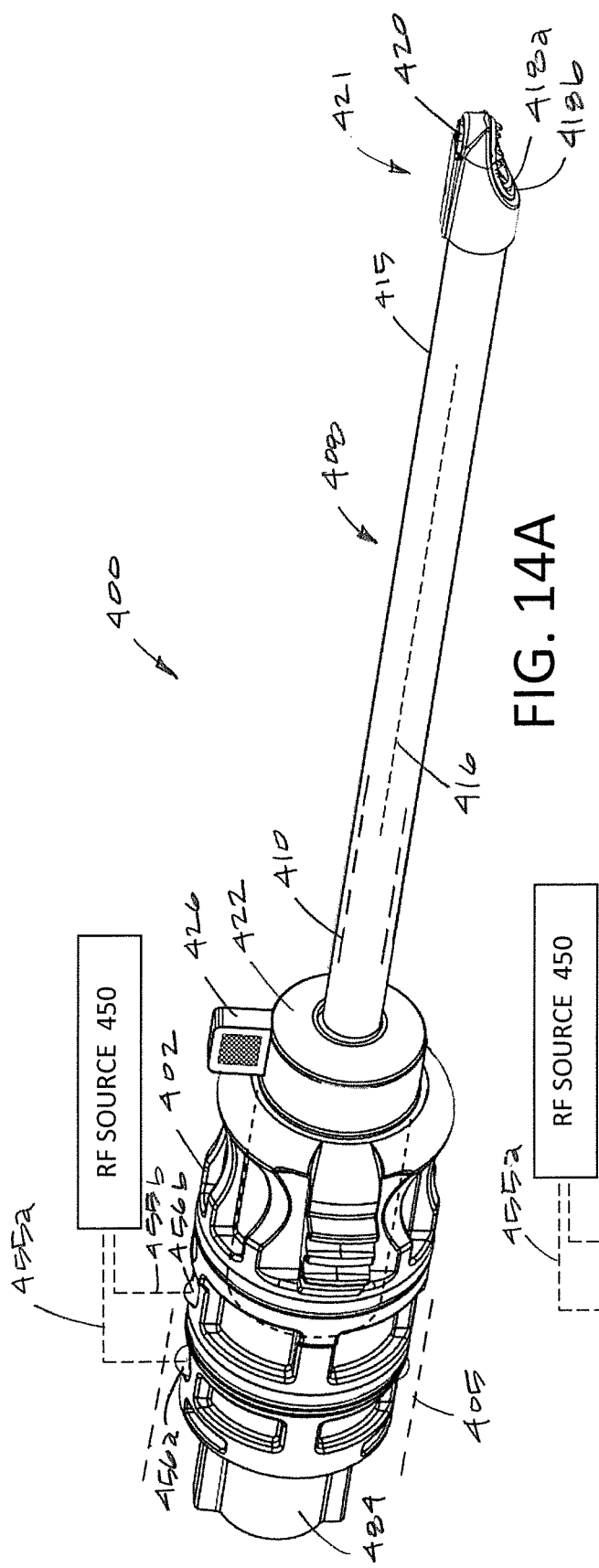
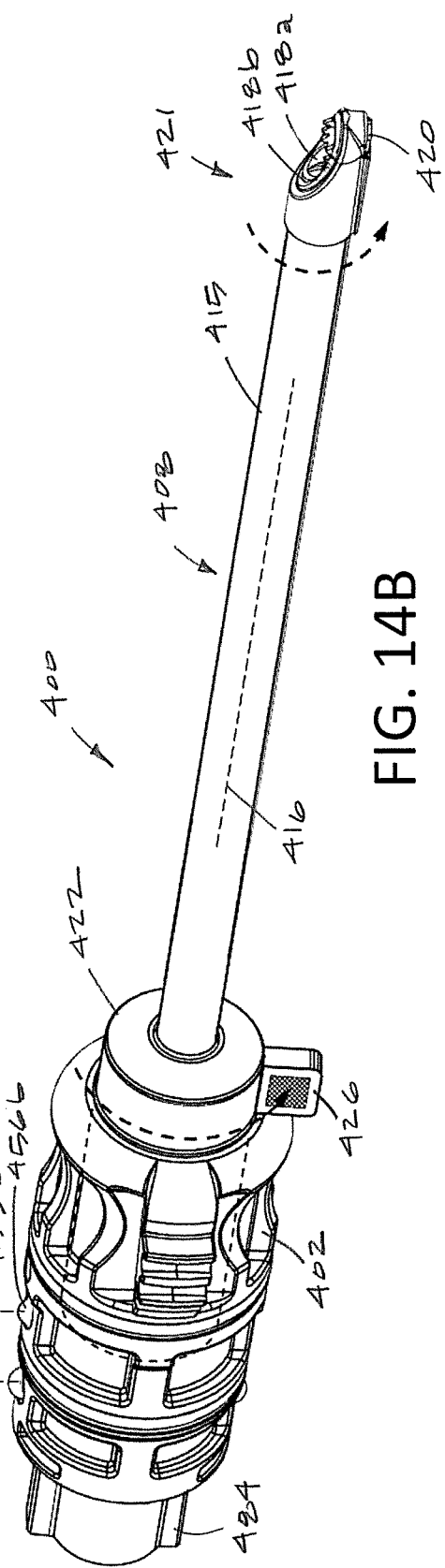
FIG. 14A
FIG. 14B

ARTHROSCOPIC DEVICES AND METHODS

CROSS-REFERENCE

This application claims the benefit of provisional application 62/869,472, filed on Jul. 1, 2019, the full disclosure of which is incorporated herein by reference.

BACKGROUND OF THE INVENTION

1. Field of the Invention

This invention relates to a medical system that includes variations of motor-driven arthroscopic shavers that carry RF electrodes for ablating or coagulating tissue.

2. Description of the Background Art

In arthroscopic procedures including subacromial decompression, anterior cruciate ligament reconstruction involving notchplasty, arthroscopic resection of the acromioclavicular joint and other similar procedures, there is a need for cutting, removal and/or contouring of soft tissue. Currently, surgeons use arthroscopic shavers and burrs having rotational cutting surfaces to remove soft tissue and bone in such procedures. Additionally, surgeons use electrosurgical ablation devices for ablating, coagulating or contouring soft tissue.

To promote efficiency, arthroscopic tool systems for mechanical cutting of soft tissue include a reusable motor-drive hand piece and interchangeable probes or shaver blades having different working ends for use in different aspects of a procedure. Typically, the electrosurgical devices consist of separate hand-held probes that are used independently of the motor-drive hand piece. Thus, in a typical arthroscopic procedure, the physician must exchange the tools frequently which is inefficient and potentially could increase the chances of introducing infectious agents into the working space.

To address this concern, mechanical cutting tools, such as shaver blades or burrs, have been combined with electrosurgical electrodes capable of coagulating or ablating tissue. Such cutting tools may also include an integrated aspiration mechanism for extracting resected tissue, irrigation fluid and ablation debris. Examples of such systems include US2019/0328417; US2019/0321095; US2019/0321063; US2019/0008538; US2018/0303509; US2018/0263649; and US2017/0252099, commonly assigned with the present invention and the full disclosures of which are incorporated herein by reference.

Some combination mechanical cutting and electrosurgical tools can require the physician to reposition the too during a procedure to selectively orient the cutter or the electrode adjacent target tissue. For example, a working end of a combination device may include a cutting window on one side and a diametrically opposed electrode on the other side. When using such a combination device in a procedure, the physician might want to switch multiple times between cutting using the cutting window and coagulation using the electrode. To make such a change, the physician would have to either rotate the device in his or her hand making the handle controls inaccessible or detach a shaft of the device from the handle, rotate the shaft about its axis, and reattach the shaft to the handle. Neither of these options is practical.

In view of the foregoing, it can be understood that that there is a need for improved combination mechanical/electrosurgical probes for use in arthroscopy and elsewhere. In particular, it would be desirable to provide combination mechanical/electrosurgical probes with improved ease of use characteristics such as simplification of the manipulations necessary to reposition the cutting and electrosurgical elements during a procedure. At least some of these objectives will be met by the inventions described hereinafter.

SUMMARY OF THE INVENTION

In a first aspect, the present invention provides an arthroscopic system comprising a hand piece with a motor drive and an elongate shaft assembly detachably secured to a distal end of the hand piece. The elongate shaft assembly includes an outer sleeve and an inner sleeve rotatably mounted in the outer sleeve. The inner sleeve couples to the motor drive when the elongate shaft assembly is attached to the hand piece, and an inner distal cutting window on the inner sleeve is configured to move in and out of alignment with an outer distal cutting window on the outer sleeve as the motor drive rotates the inner sleeve. A distal electrode on an outer surface of the outer sleeve is positioned at a location opposite to that of the outer distal cutting window, and the outer sleeve member is rotatable relative to the hand piece when the hub is secured to the hand piece. Thus, a user can hold the hand piece in one hand and rotate the outer sleeve to selectively place the outer distal cutting window or the distal electrode in an upward orientation relative to the user while continuing to hold the hand piece in the one hand. The design allows the user to rotate the outer sleeve with the same hand holding the handle or alternatively to use the other hand. In both cases, the handle orientation in the first hand remains the same with access to controls remaining unchanged.

In particular embodiments, the electrode may comprise an active electrode. In such embodiments, a return electrode is typically carried by the shaft assembly.

In particular embodiments, the distal electrode and the outer distal cutting window are rotationally spaced-apart by 175° to 195°, typically by 180°, relative to a longitudinal axis of the shaft.

In other embodiments, the arthroscopic systems of the present invention may further include an actuator coupled to the outer shaft member configured for rotating the outer shaft member between the first and second rotational orientations. For example, the actuator may comprise a rotating core having a grip tab, wherein the rotating core is rotatably attached to a distal end of the hub.

In still other embodiments, the arthroscopic system of the present invention may further comprise an RF source operatively connected to the electrode. The RF source may connect to the electrode through electrical contacts in the hand piece that engage cooperating electrical contacts in the hub.

Alternatively, the RF source may connect to the electrode through an electrical cable external to the hand piece. As a further alternative, the RF source may connect to the electrode through an electrical cable coupled to the hub.

In yet further embodiments, the arthroscopic systems of the present invention may further comprise a first sensor system for sensing the rotational orientation of the outer shaft member relative to the hub when coupled to the hand piece. The first sensor system may comprises a first sensor carried by the hand piece adapted to sense a magnetic field of at least one magnet carried by the rotatable outer shaft member. Foe example, the first sensor may comprise a Hall sensor. Such embodiments may further comprise a second sensor system for sensing the rotational orientation of the inner shaft member relative to the outer shaft member. In such instances, the second sensor system may comprise a second sensor carried by the hand piece adapted to sense a magnetic field of at least one magnet carried by the inner shaft member. For example, the second sensor may comprise a Hall sensor.

Arthroscopic systems comprising one or more sensors will often further comprise a controller operatively coupled to the motor drive, the RF source, and the first and/or second sensors, together with a controller algorithm adapted to actuate the motor drive to rotate the inner shaft member to a selected position in response to the outer shaft member being rotated to the first or second rotational orientation. The controller algorithm is typically further adapted to disable the RF source in response to the inner shaft member not being in said selected position.

In a second aspect, the present invention provides method performed by a user comprising providing a probe including a hand piece with a motor drive detachably coupled to an elongated shaft assembly. The elongated shaft assembly typically includes an outer sleeve with an outer distal cutting window, a distal electrode, and an inner sleeve with an inner distal cutting window. A working end of the probe is introduced into a treatment space with the hand piece being held in the user's hand. The outer sleeve is rotated about a longitudinal axis of the hand piece while the user holds but does not rotate the hand piece to selectively position either the outer distal cutting window or the distal electrode adjacent to a target tissue site in the treatment space. The outer distal cutting window is engaged against the targeted tissue, and the motor drive is actuated to rotate the inner sleeve to resect the target tissue site when the outer distal cutting window is adjacent to the target tissue site. RF or other electrical current is delivered to the distal electrode when the distal electrode is located adjacent to the target tissue. Operation of the motor drive and/or of the current delivery is typically accomplished by the user with the hand that holds the hand pieces using controls on the hand pieces. The controls remain accessible as the hand piece does not need to be reoriented to reposition the cutting window and the distal electrode.

In specific aspects of the methods, the user typically manipulates the hand piece without rotating the elongated shaft assembly about the longitudinal axis of the hand piece. Usually, the user manually rotates the outer sleeve while holding the hand piece. For example, the user may manually rotate a rotating core which is rotatably attached to a distal end of the hub. The rotating core may have a grip tab and may be manipulated by one hand while holding the hand piece with the other hand. Alternatively, the user may manually rotate a rotating core rotatably attached to a distal end of the hub and having a grip tab with one hand while holding the hand piece with the same hand.

The arthroscopic methods of the present invention may further comprise sensing the rotational orientation of the outer shaft member relative to the hand piece with a sensor and controlling the motor drive to rotate the inner shaft member to a selected position relative to the outer shaft member with a controller coupled to the sensor. Typically, the controller limits energy delivery to the distal electrode when inner shaft member is not in said selected position.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

FIG. 14A is a perspective view of another probe variation that has an outer sleeve carrying an electrode arrangement together with a mechanism that allows for rotation of the outer sleeve relative to the handle and locking the hub of the probe, with the electrode arrangement of the probe shown in a first rotational position.

FIG. 14B is a perspective view of the probe of FIG. 14A in a second rotational position with the electrode arrangement rotated 180°.

DETAILED DESCRIPTION OF THE INVENTION

The present invention relates to arthroscopic shavers, tissue cutting devices and related methods of use. Several variations of the invention will now be described to provide an overall understanding of the principles of the form, function and methods of use of the devices disclosed herein. In general, the present disclosure provides for variations of arthroscopic tools adapted for cutting soft tissue and for RF ablation and/or coagulation. The arthroscopic tools are typically disposable and are configured for detachable coupling to a non-disposable hand piece that carries a motor drive component. This description of the general principles of this invention is not meant to limit the inventive concepts in the appended claims.

Figure 1:
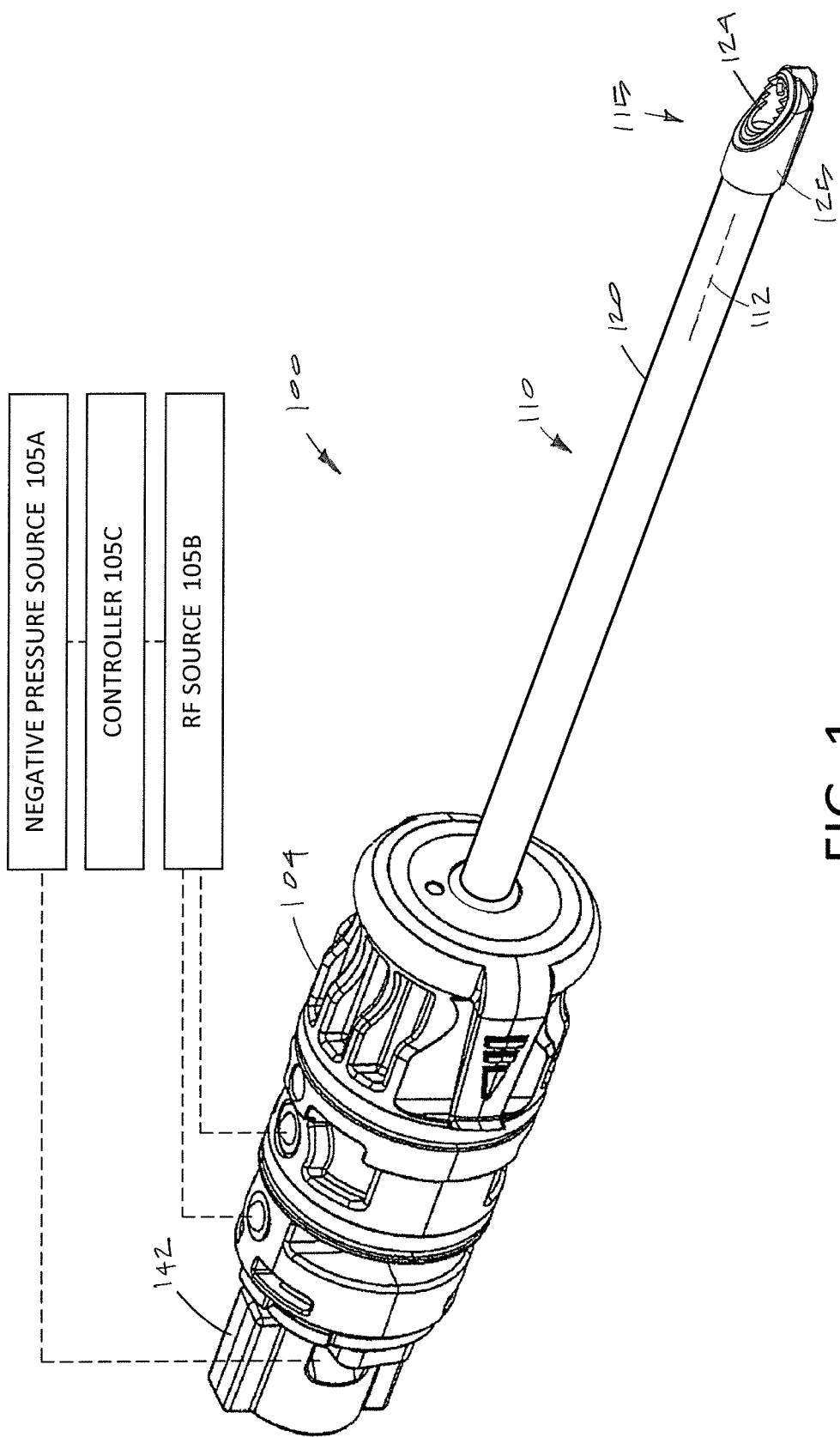
FIG. 1 is a perspective view of a disposable arthroscopic cutting probe that is adapted for detachable coupling to a motor drive hand piece were in the working end includes a rotating shaver blade in the ceramic housing carried an active electrode.
Figure 2:
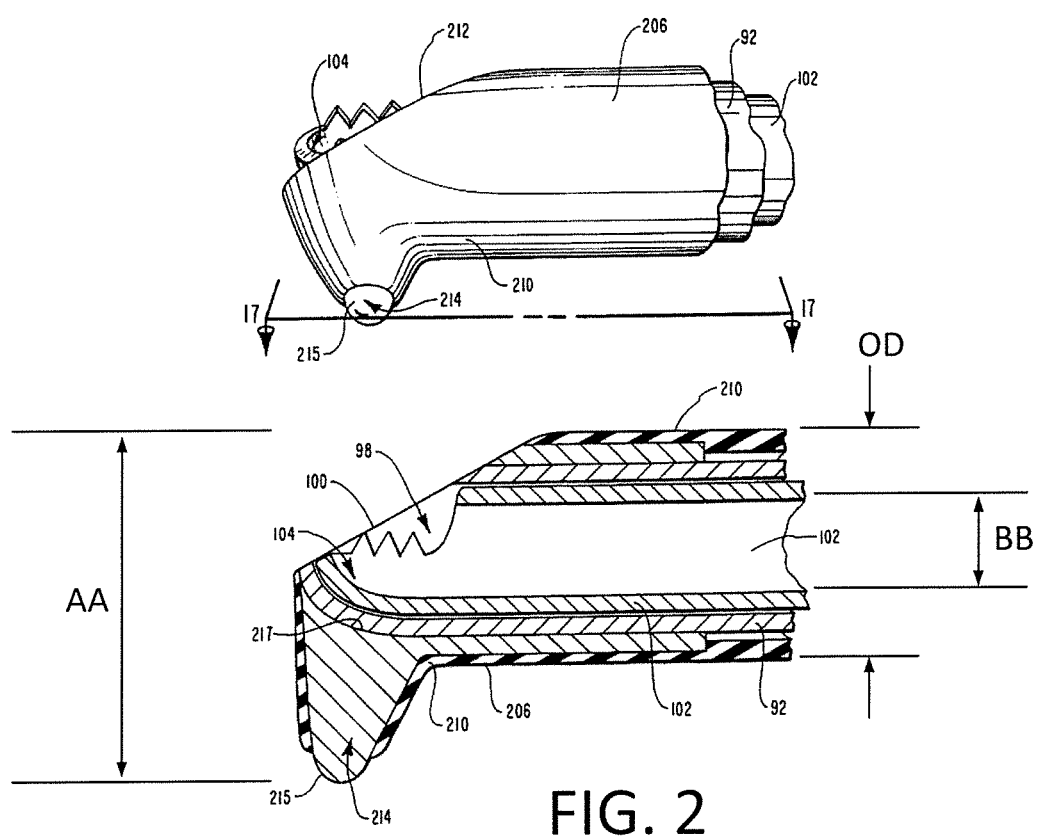
FIG. 2 is a prior art working end of a rotating cutter that carries an electrode arrangement as in U.S. Pat. No. 5,364,395 to West.
Figure 3:
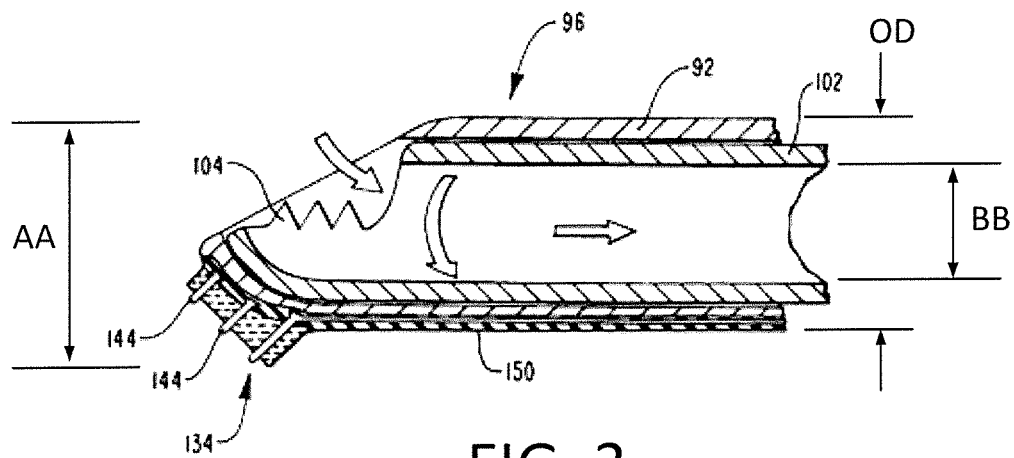
FIG. 3 is another prior art working end of a rotating cutter that carries an electrode arrangement as in U.S. Pat. No. 5,904,681 to West.
Figure 4:
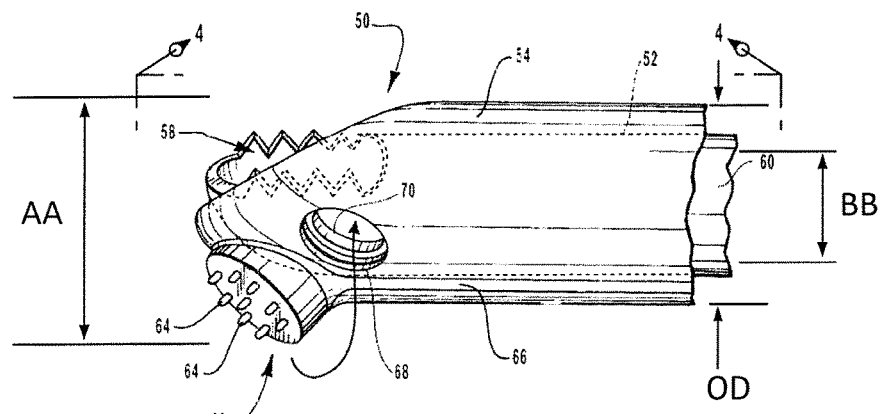
FIG. 4 is yet another prior art working end of a rotating cutter that carries an electrode arrangement as in U.S. Pat. No. 6,610,059 to West.
Figure 5:
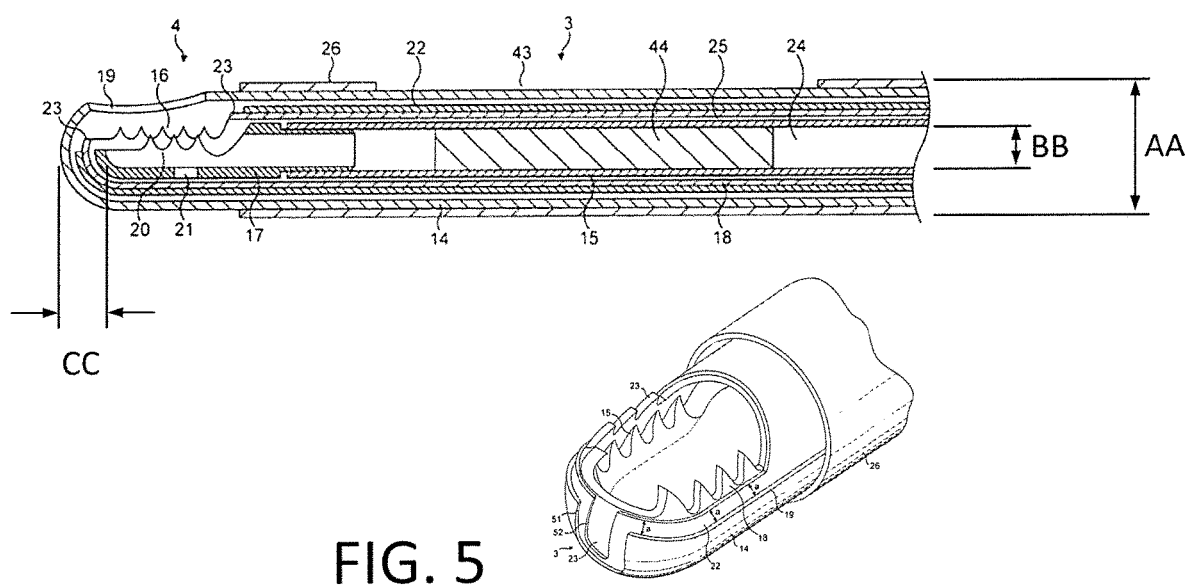
FIG. 5 is the another prior art working end of a rotating cutter that carries an electrode arrangement as in U.S. Pat. No. 7,699,846 to Ryan.
Figure 6A:
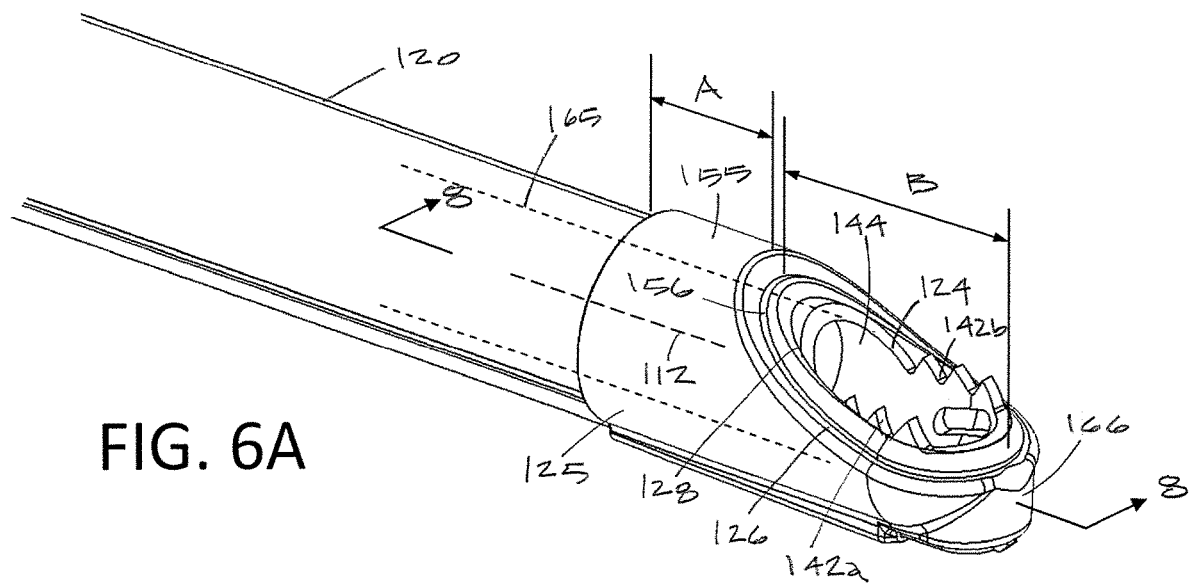
FIG. 6A is an enlarged perspective view of the working end of the probe of FIG. 1 showing the ceramic housing coupled to the outer sleeve and a rotating inner cutter when the electrode is hidden from view the opposing side of the ceramic housing.
Figure 6B:
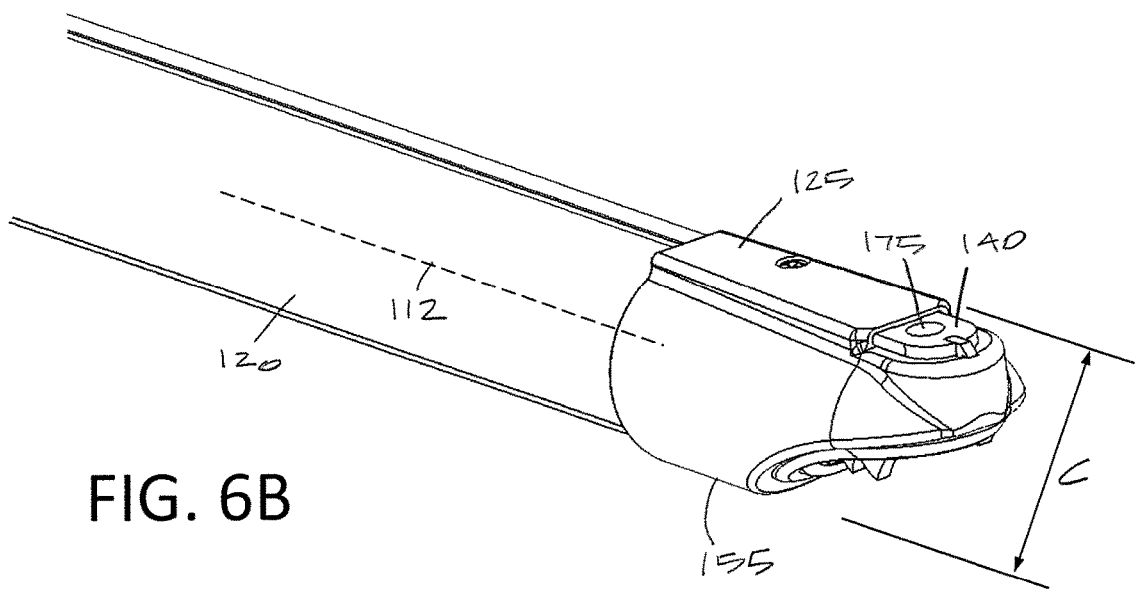
FIG. 6B is an enlarged perspective view of the working end FIG. 6A rotated 180° to show the electrode carried by the ceramic housing.

In one variation shown in FIGS. 1, 6A and 6B, a disposable shaver or probe 100 of the invention has a proximal hub 104 (FIG. 1) that can be received by a receiver or bore in an arthroscopic hand piece that carries a motor drive. Such motor drive hand pieces may be further described in the following co-pending and commonly owned patent applications: Ser. No. 15/271,184 filed Sep. 20, 2016 titled ARTHROSCOPIC DEVICES AND METHODS; Ser. No. 15/410,723 filed Jan. 19, 2017 titled ARTHROSCOPIC DEVICES AND METHODS; Ser. No. 15/454,342 filed Mar. 9, 2017 titled ARTHROSCOPIC DEVICES AND METHODS; and Ser. No. 15/483,940 filed Apr. 10, 2017 titled ARTHROSCOPIC DEVICES AND METHODS.

In one aspect, the probe 100 has a working end 115 that carries a high-speed rotating cutter that is configured for mechanical tissue cutting in many arthroscopic surgical applications, including but not limited to cutting tissue in shoulders, knees, hips, wrists, ankles and the spine. Further, the probe includes a bi-polar electrode arrangement for ablating tissue with plasma in a saline environment as is known in the art. Referring to FIG. 1, the hub 104 of the probe 100 is adapted for coupling to a negative pressure source 105A, an RF source 105B and a controller 105C as also described in the above co-pending patent applications.

In FIGS. 1 and 6A, it can be seen that probe 100 has a shaft or shaft assembly 110 extending along longitudinal axis 112 to the working end 115. The shaft assembly 110 comprises an outer sleeve 120 and an inner sleeve 122 (FIG. 8) rotatably disposed therein. The inner sleeve 122 has a distal cutting portion or member 124. The outer sleeve 120 carries a distal dielectric body or housing 125 (typically called ceramic housing 125 herein) with a window 126 therein that surrounds an outer window 128 in the outer sleeve 120. An electrode 140 is carried on the ceramic housing 125 on the side opposing the window 126 in the ceramic housing. The shaft assembly 110 extends from the proximal hub 104 wherein the outer sleeve 120 is coupled in a fixed manner to the hub 104 which can be an injection molded plastic, for example, with the outer sleeve 120 insert molded therein. The inner sleeve 122 is coupled drive coupling 142 (FIG. 1) that is configured for coupling to the rotating motor shaft of the motor drive hand piece.

More in particular, referring to FIG. 6A, the rotatable cutting member 124 is a metal cutter with sharp cutting edges 142a and 142b on opposing sides of inner window 144 in the cutting member 124 for cutting soft tissue. The motor drive is operatively coupled to the cutter to rotate the cutting member at speeds ranging from 1,000 rpm to 20,000 rpm.

Figure 8:
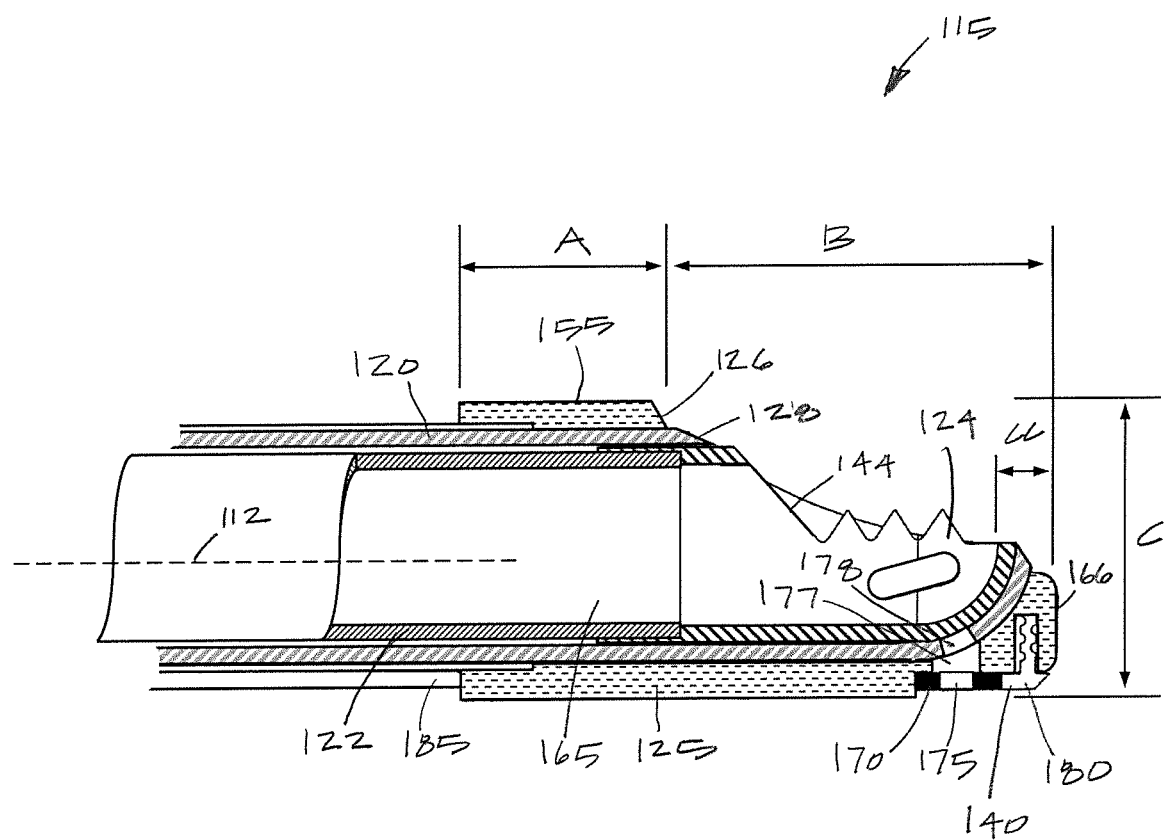
FIG. 8 is a sectional view of the working end of FIG. 6A taken along 8-8 of FIG. 6A showing the ceramic housing coupled to the outer sleeve, an active electrode carried the surface of the ceramic housing and a rotating inner cutter.

In one aspect of the invention referring to FIGS. 6A, 6B and 8, the ceramic housing 125 is adapted to be extremely strong and durable besides providing a dielectric base for carrying the electrode 140. As described above, the working end 115 may be used as a lever between bones in a joint and therefore the ceramic has to be extremely durable. Thus, one means of providing a durable ceramic housing 125 is to have a collar portion 155 of the ceramic housing 125 extending 360° around the outer sleeve 120. Further, the ceramic housing 125 and window 126 therein extends entirely around the window 128 in the outer sleeve 120 and can be secured to the outer sleeve 120 with adhesives or an otherwise very tight fit. For additional strength, the collar portion 155 as an axial length A that is long enough to strengthen the housing 125, wherein such axial length A can be at least 0.10" as further described below. Stated another way, the axial length A of the collar portion 155 of the ceramic housing 125 is at least 25% of the length B of the window 126 in the ceramic housing 125 (see FIG. 6A). More often, the axial length A of the collar 155 is at least 35% of the axial length B of the ceramic window 126.

In general, an arthroscopic probe of corresponding to invention consists of an elongated shaft comprising outer and inner sleeves, 120 and 122, of an electrically conductive material extending about an axis 112 to a working end 115, the sleeves configured with respective outer and inner resecting windows in the working end, a ceramic body 125 of the working end having a collar portion 155 extending in 360° around a region of the outer sleeve 120 proximal to the outer resecting window 128, and an RF electrode 140 disposed on an outer surface of the ceramic body spaced apart from the outer resecting window. In one variation, the collar portion 155 has an axial length of at least 0.10", at least 0.15", at least 0.20" or at least 0.25".

Further, the arthroscopic probe 100 has a distal ceramic housing 125 with the collar portion 155 as described above wherein the wall thickness of the ceramic collar 155 surrounding the outer sleeve 120 is at least 0.005", at least 0.010" or at least 0.015".

Further, still referring to FIGS. 6A and 6B, the working end 115 has an insertion profile with a maximum cross-section dimension indicated at C in FIG. 6B of less that 6.5 mm or more often less than 5.5 mm. In one variation, the ceramic housing 125 is fabricated from a ceramic selected from the group of Alumina, Zirconia, an Alumina-Zirconia composite, Silicon Nitride, Silicon Carbide, synthetic Ruby and synthetic Sapphire.

In another aspect of the invention, the ceramic body 125 is fabricated such that the window 126 therein has is small radiuses or chamfers 156 in the window edges (FIG. 6A) so that such ceramic window edges are set back from the metal edges of window 128 in outer sleeve 120 by a small dimension, for example, between 0.005" and 0.10". Thus, the assembly of the outer sleeve 120 and the closely fitting ceramic housing 125 are configured to be strong and durable.

In another aspect of the invention, the bore or passageway 165 in inner sleeve 122 that communicates with negative pressure source 105A is relatively large relative to the insertion profile C of the working end 115 (see FIGS. 6A-6B and 8). In one variation, the ratio of the cross-section of the bore 165 relative to the insertion profile cross-section C is at least 0.5:1 or at least 0.6:1. As can be seen in FIG. 8, a further advantage of the working end is that the distal edge of the cutting member 124 is spaced close to the distal tip 166 of probe indicated at CC in FIG. 8, for example less than 0.15".

Figure 7A:
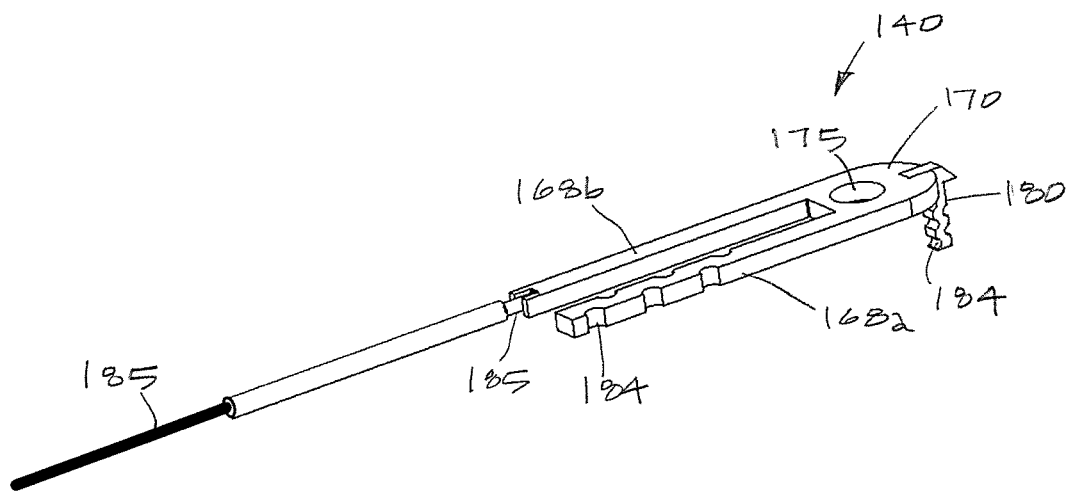
FIG. 7A is a perspective view of the active electrode of FIG. 6B shown removed from the ceramic housing.
Figure 7B:
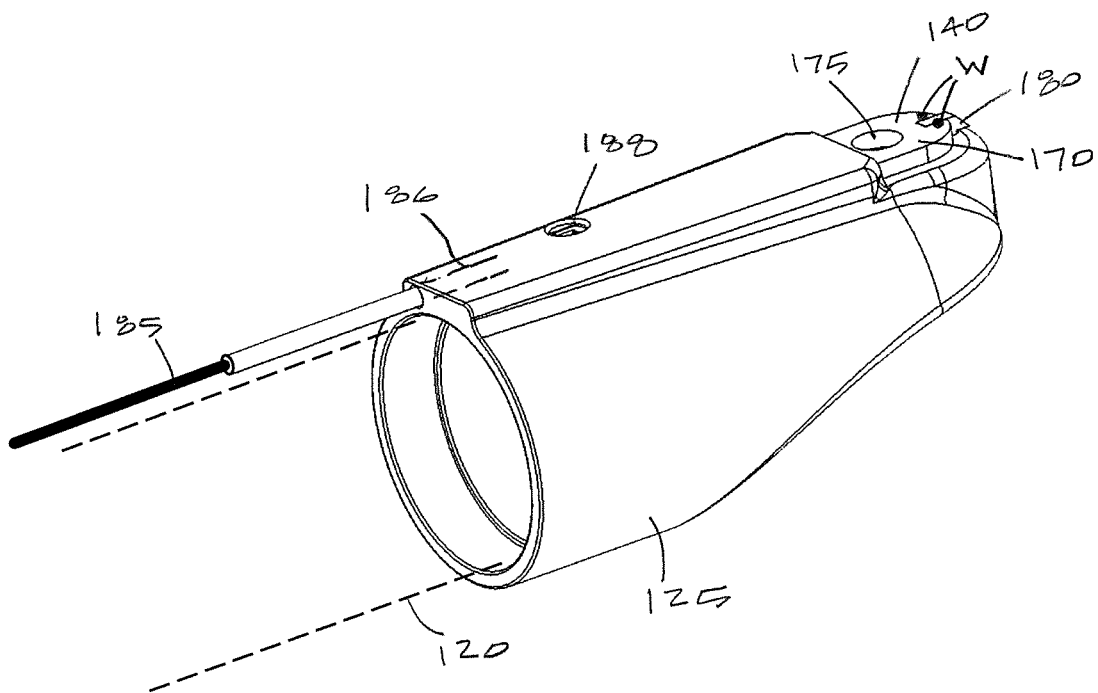
FIG. 7B is a perspective view of the working end of FIG. 6B showing the assembly of the ceramic housing and active electrode with the outer sleeve in phantom view.

Now turning to FIGS. 7A and 7B, in another aspect of the invention, the probe includes means for securing electrode 140 to the ceramic housing 125. As described previously, very durable connections are required between the electrode 140 and the ceramic housing 125. FIG. 7A shows electrode 140 separated from the ceramic housing 125 wherein the electrode has first and second anchor portions or legs 168a and 168b that are adapted for insertion into axially-extending bores or slots in the ceramic housing 125 (not visible). Further, an exposed portion 170 of electrode 140 includes an aperture 175 that communicates with an aperture 177 in the ceramic body which in turn communicates with aperture 178 in the outer sleeve 120 (see FIG. 8).

A separate metal pin 180 for securing the electrode is provided for insertion into a receiving bore 182 in the ceramic body 125 as can be seen in FIG. 8. Thus, in FIG. 7B, it can be understood that the electrode legs 168a and 168b can be inserted through receiving channels in the ceramic body 125 and can be further glued in place with notches 184 in a leg (and metal pin 180) adapted for holding an adhesive. The metal pin 180 can be inserted into bore 182 and then welded to the electrode 140 (see welds W in FIG. 6B) to secure the electrode in the ceramic housing 125.

Still referring to FIGS. 7A-7B, an electrical lead 185 then can be inserted through channel 186 in the ceramic body 125 to connect with electrode leg 186b. An opening 188 in the ceramic body 125 is provided to weld or solder the electrical lead 185 to electrode leg 186b. Thereafter, a potting material can be used to fill in the opening 188 to cover the electrical connection. In one aspect of the invention, the anchor shaft or leg portions 186a, 186b of the electrode 140 have a mean cross sectional dimension of at least 0.005" wherein such minimum dimensions are provided to prevent rapid erosion and burnout of the electrode.

Figure 9:
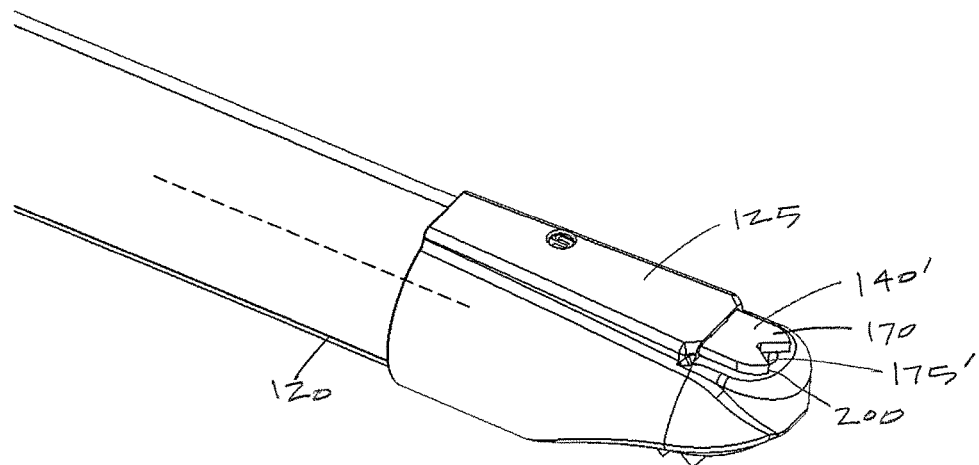
FIG. 9 is a perspective view of another working end similar to that of FIGS. 6A-6B with an active electrode that is cantilevered from slots in the ceramic housing.
Figure 10:
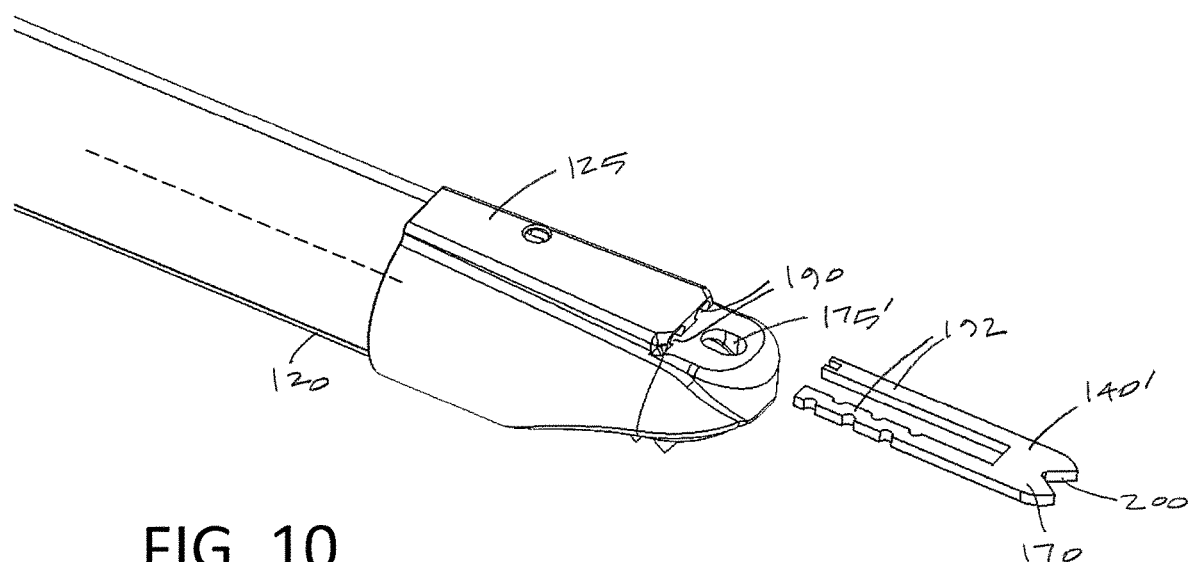
FIG. 10 is a perspective view of the working end of FIG. 9 in an explode view with the active electrode separated from the ceramic housing.

FIGS. 9 and 10 illustrate another embodiment of the working end 115 wherein the ceramic housing 125 has an electrode 140' that is adapted to cantilever from slots 190 in the ceramic housing 125. In this variation, the working end 115 does not require the additional metal pin 180 of FIG. 8 to secure the electrode to the ceramic housing 125 in a durable manner.

In general, an arthroscopic probe of the invention comprises an elongated shaft including outer and inner sleeves of an electrically conductive material extending about an axis to a working end of the shaft, the outer and sleeves configured with respective outer and inner resecting windows in the working end, a ceramic body carried by the outer sleeve at the working end, and an RF electrode disposed on the ceramic body wherein the RF electrode comprises an active surface portion and an anchor shaft portion disposed in an axial channel in the ceramic body configured to secure the RF electrode in the ceramic body. In one variation, the active surface portion of the electrode is cantilevered from the axial channel by at least 0.10" over a portion of the ceramic body. In a variation, the active surface portion of the electrode is cantilevered over an aperture in the ceramic body that communicates with a passageway in the shaft that is coupled to a negative pressure source.

Figure 11:
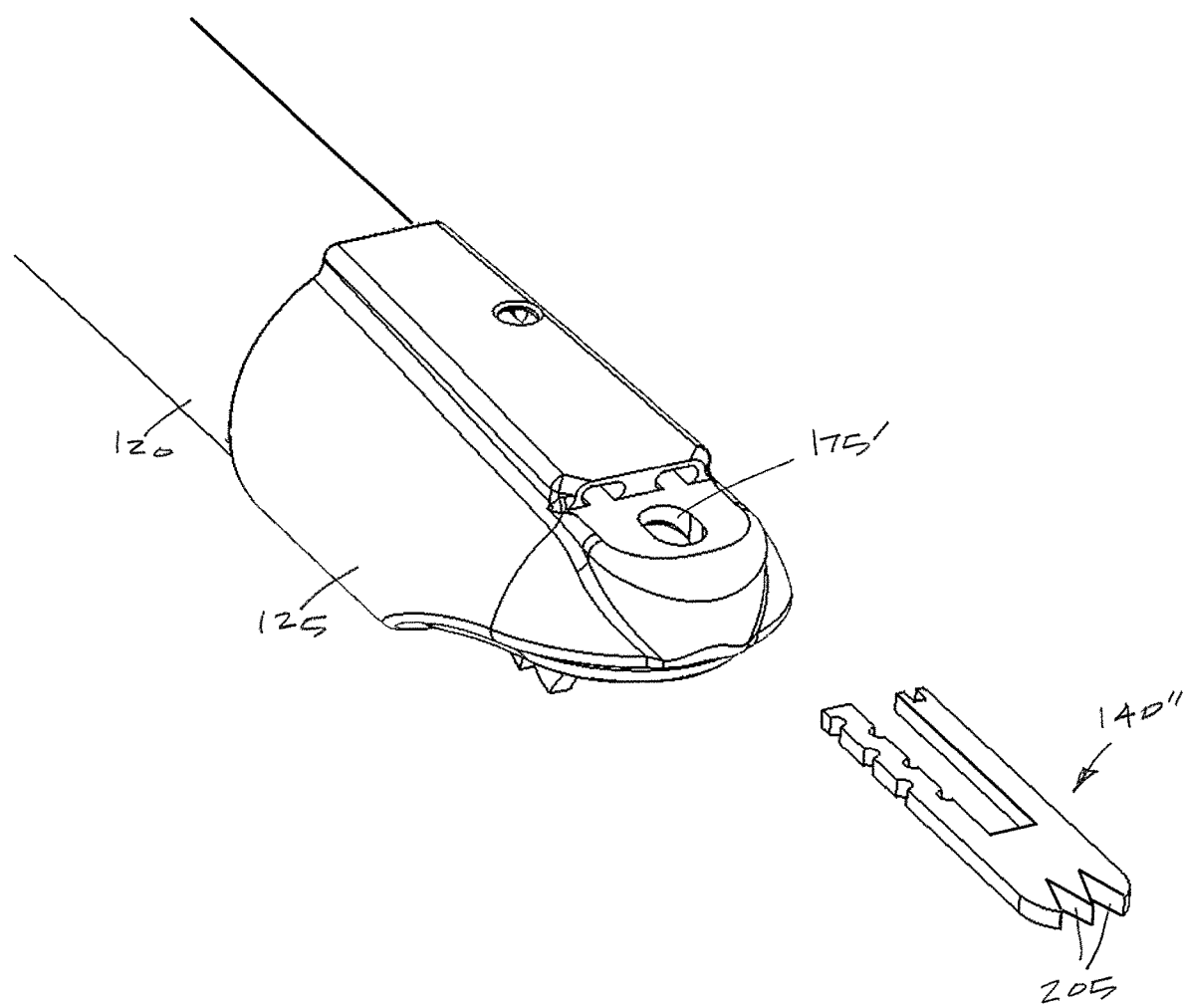
FIG. 11 is a perspective exploded view of another working end similar to that of FIG. 9 showing the active electrode separated from the ceramic housing.

In another aspect of the invention referring to FIGS. 10 and 11, the ceramic body 125 is configured with at least one slot 190 receiving an anchor portion 192 of an electrode 140' or 140" wherein the dimensions of the slot 190 are adapted to closely fit the dimensions of the electrode anchor portion 192 to thereby prevent plasma migration into the slot 190 which could the erode and burnout the electrode. In one variation, the gap dimension between the surface of the anchor portion 192 and the anchoring bore 190 is 0.050" or less, and more often 0.020" or less.

In general, an arthroscopic RF device of the invention for operating in a saline environment comprises an elongate sleeve extending about an axis to a distal dielectric body, an electrode carried by the dielectric body connected to an RF source having operating parameters for generating a tissue-ablating plasma around the electrode in the saline environment, wherein the electrode comprises an exposed surface portion and an anchor portion positioned in an anchoring bore in the dielectric body and wherein the cross section of the anchor portion is sufficiently tightly fitted in the cross section of the anchoring bore to prevent plasma formation around the anchor portion in the anchoring bore. Further, the portion of anchor portion 192 in the bore 190 with the tight gap dimension has a length of at least 0.20".

In another aspect of the invention, as can be seen in FIG. 10, the exposed surface portion 170 of the electrode 140 extends partly across the aperture 175' in the ceramic housing 125 wherein the electrode has a non-linear edge 200 extending across such aperture 175'. In one variation shown in FIG. 10, the electrode has a v-shaped edge extending over the aperture 175'. During use, the v-shaped edge 200 of the electrode 140 is adapted to ignite plasma faster due to a known "RF edge effect" and further the additional length of the two edges of the v-shape can erode more slowly during use than a shorter linear edge. During use, the erosion of electrode edge 200 then exposes a larger portion of the aperture 175' in the ceramic body 125. This is been found to be advantageous during use wherein the increasing exposure of aperture 175' in the ceramic housing 125 is adapted to the increase the efficiency of aspirating bubbles away from the energized electrode 140'. FIG. 11 shows a similar electrode 140" with a two v-shaped edges 205 that are adapted to extend across the aperture 175' in the ceramic body 125 for similar purposes.

In general, an arthroscopic RF device for operating in a saline environment comprises an elongate sleeve extending about an axis to a distal dielectric body, an electrode carried by the dielectric body connected to an RF source having operating parameters for generating a tissue-ablating plasma around the electrode in the saline environment, a rotatable member with a distal cutter rotatably disposed in sleeve, and an aperture in the dielectric body that communicates with a passageway in device coupled to a negative pressure source wherein the electrode prior to use has an exposed surface portion that extends partly across the aperture and thereby partly occludes the aperture. In one variation, the electrode prior to use occludes less than 80% of the aperture. In other variations, the electrode prior to use occludes less than 70% of the aperture, less than 60% of the aperture or less than 50% of the aperture. Further, the exposed surface portion of the electrode has a non-linear edge that extends partly across the aperture, which in one variation the electrode has a v-shape in the edge that extends partly across the aperture. In another variation, the electrode has a plurality of v-shapes in the edge that extends partly across the aperture.

In another variation, an arthroscopic device with the invention comprises an elongated shaft assembly have an insertion profile having a cross-sectional dimension, the shaft assembly comprising (i) an outer sleeve extending to a working end with a first window, (ii) an inner sleeve rotationally disposed in the outer sleeve with a second window communicating with a tissue extraction channel therein, and (iii) a ceramic body affixed to the outer sleeve and an electrode carried by the ceramic body wherein the electrode has a thickness of at least 0.005" and a surface area of at least 0.10 sq. inches and wherein the electrode is spaced apart from the conductive outer sleeve by a ceramic body having a thickness of at least 0.010". In this variation, the electrode comprises a surface portion and an anchor portion, wherein the anchor portion is disposed in an anchoring channel in the ceramic body per housing where the gap between surfaces of the anchor portion and anchoring channel is sufficiently small so as to choke plasma formation around said anchor portion.

Figure 12:
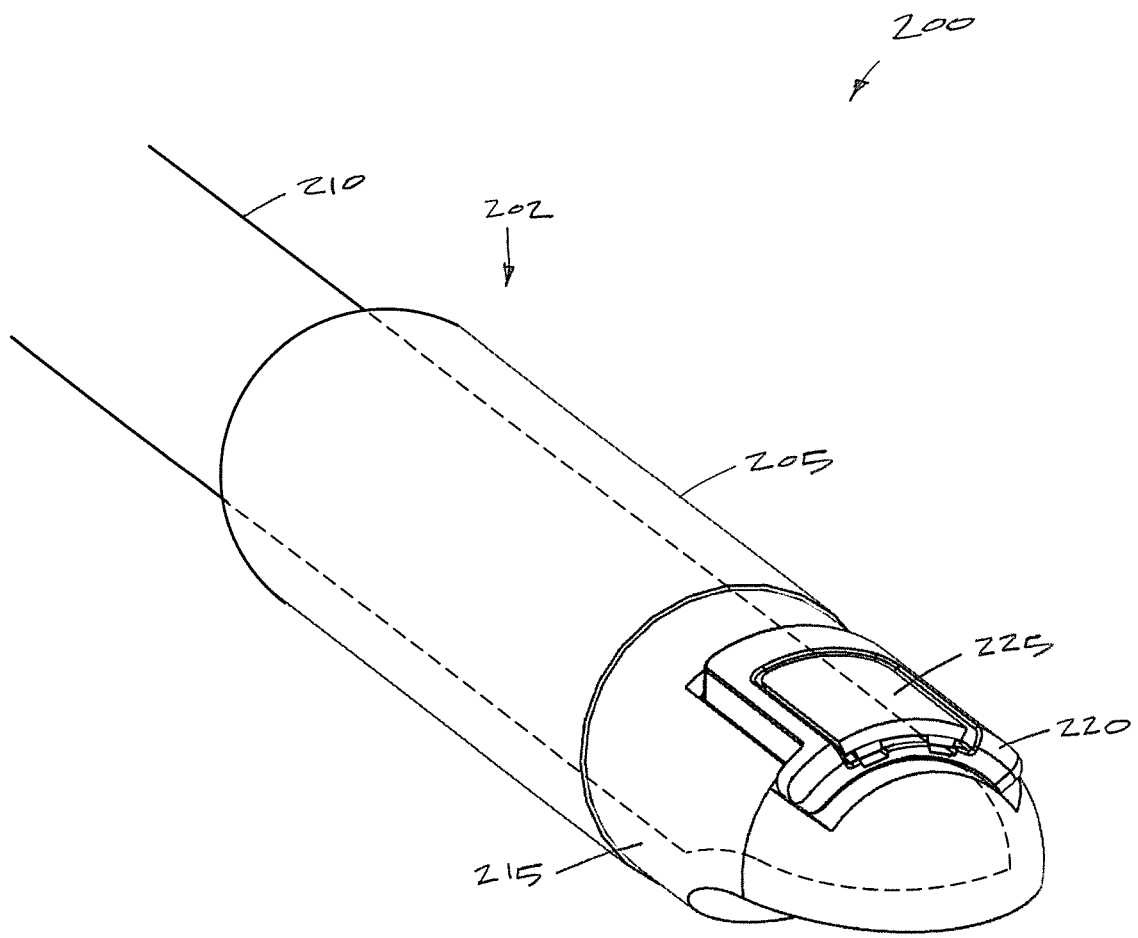
FIG. 12 is a perspective view of another working end with features similar to that of FIGS. 9-10 except that the electrode is carried in a ceramic insert that is received by a channel in a metal outer sleeve instead of the ceramic housing of FIGS. 9-10.
Figure 13:
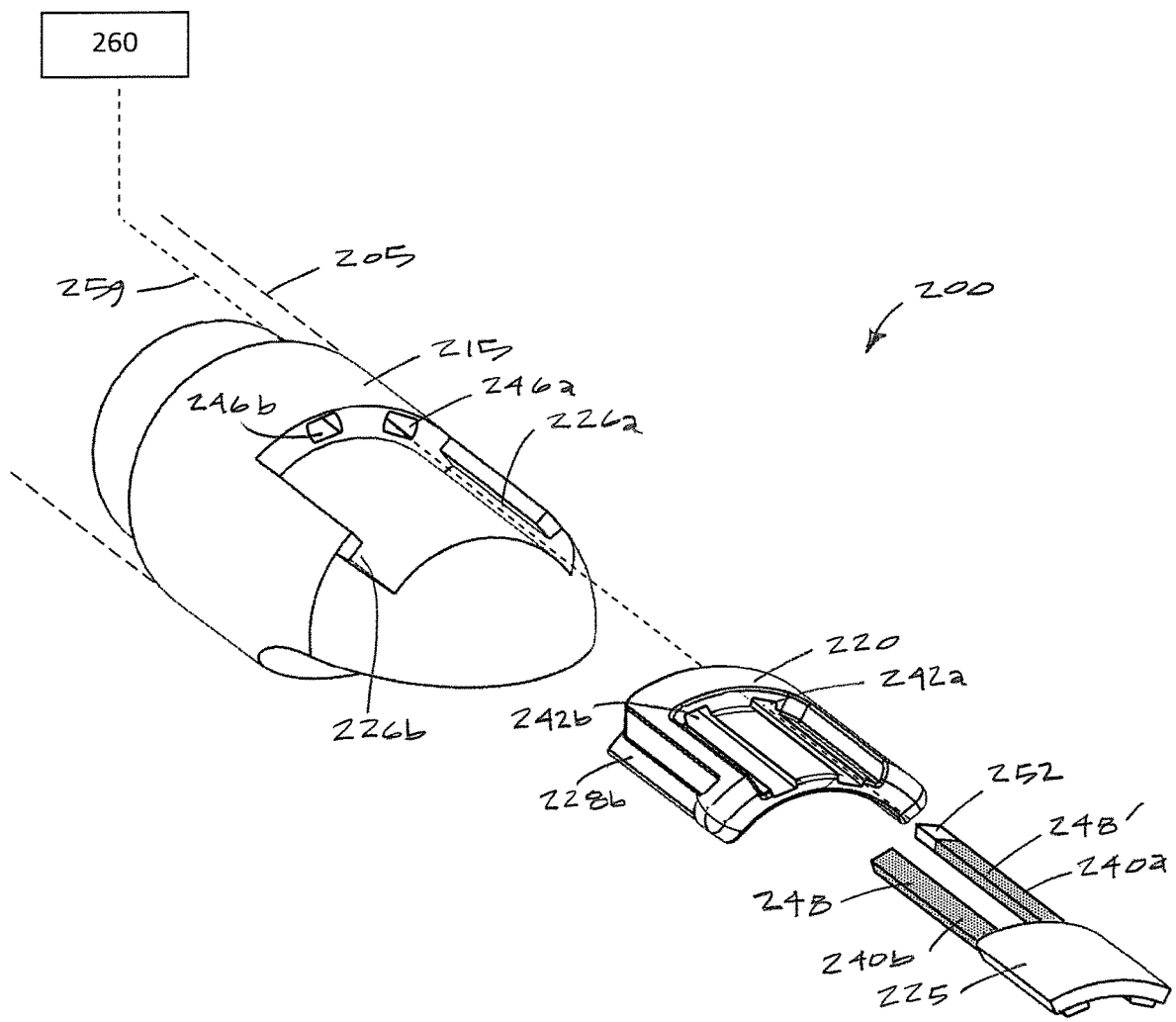
FIG. 13 is a perspective exploded view of the working end of FIG. 12 showing the active electrode, ceramic insert and a metal sleeve with a distal end having a window therein.

FIG. 12 illustrates the working end 200 of another probe shaft 202 with an outer sleeve 205 that extends from a hub similar to that of FIG. 1. An inner sleeve 210 rotates in the outer sleeve 205 as described previously for cutting soft tissue with cooperating cutting windows in the inner and outer sleeves. The outer sleeve 205 typically is a metal such as stainless steel that terminates in a conductive metal housing portion 215 shown in FIG. 12. The metal housing 215 is configured to receive a dielectric or ceramic insert 220 that carries an active electrode 225. In the variation of FIGS. 12-13, the dielectric the 220 is received by lateral channels 226a and 226b in the metal housing 215 that cooperate with the lateral edges 228a and 228b of the dielectric insert 220 (see FIG. 13). This variation differs from previous embodiments wherein the working end 115 of the outer sleeve 120 consisted of a larger ceramic housing 125 that carries the active electrode 140 (see FIGS. 6A-6B).

FIG. 13 is an exploded view of the working end of FIG. 12 showing the metal portion 215 of the outer sleeve 205, the dielectric insert 220 and the active electrode 225. It can be seen that the electrode 225 has anchoring legs 240a and 240b adapted for extending through the cooperating bores 242a and 242b in the dielectric insert 220 and then into bores 246a and 246b in the metal housing 215. Thus, the anchoring legs 240a and 240b that cantilever the active electrode 225 are similar to variations described previously where the anchoring legs of the electrode provide substantial strength in securing electrode to the working end (see FIGS. 9-11). As can be seen in FIG. 13, the anchoring leg 240b that extends into the metal housing 215 is coated with an insulator 248. In FIG. 13, the second leg 240b is partially covered with insulator 248' with a proximal tip 252 of the anchor leg without insulation for coupling to an electrical lead 259 extending from RF source 260 through the outer sleeve 205 and metal housing 215 with a connection is covered with an insulator (not shown). This method of attaching the electrode 225 to the working end 200 has proven to be robust. Further, the variation of FIGS. 12 and 13 provides an assembly wherein the dielectric insulator, which is typically a ceramic, is not subject to stresses from bending or torsion that would occur with the embodiment of FIGS. 1, 6A and 6B where the ceramic housing 125 is fully exposed to stresses during use.

FIGS. 14A-14B illustrate another aspect of the invention which relates to a probe 400 having hub 402 that detachably couples to motor driven hand piece 405 (shown in broken line) as described previously. In this variation, a shaft assembly 408 includes an inner sleeve 410 (hidden line) that rotates in an outer sleeve 415 about a longitudinal axis 416, as in previous embodiments, for cutting soft tissue or burring hard tissue. The embodiment of FIGS. 14A-14B differs from previous embodiments described herein in that the outer sleeve 415 is manually rotatable relative to the hub 402 (in addition to the inner sleeve 410 being rotatably driven within the outer sleeve 415 by hand piece 405).

As with prior embodiments, the probe hub 402 may be removably attached and locked into an assembly of the hand piece 405 and motor drive in a particular rotational orientation, typically with a cutting windows 418a of the inner sleeve 410 and a cutting window 418b of the outer sleeve 415 facing upwardly or downwardly relative to the hand piece 405. An active electrode 420 is located on a side of a working end 421 opposite to that of the outer cutting window 418b. In prior embodiments described herein, the outer sleeve 415 and outer cutting window 418b would then remain in this orientation even as the inner sleeve 410 is rotated by the motor drive. An active electrode 420 is located on a side of a working end 421 opposite to that of the outer cutting window 418b.

With many arthroscopic shavers of the type used for soft tissue cutting, physicians prefer not to rotate the hand piece in their hand during a procedure, thus limiting the cutting windows to either an upward or downward direction, depending on the initial position in which the hand piece was grasped by the physician.

The working end 421 of the device probe 400, however, includes cutting windows 418a and 418b and an electrode arrangement 420 on opposite sides thereof to allow the physician to use two distinct functional treatment tools. The cutting windows for soft tissue resection are one side and the active electrode for tissue ablation is positioned from 175° to 195°, typically 180° apart from the cutting windows. When using this device in a procedure, the physician would typically want to switching multiple times between soft tissue resection and electrosurgical ablation. Thus, for a physician to change from soft tissue cutting to electrosurgical ablation, he or she would have to either (i) rotate the handle 405 in his or her hand to orient the desired treatment tool to interface with tissue (which many or most physicians prefer not to do), or (ii) remove the probe 400 from the hand piece 405, rotate 180° about its longitudinal axis, and re-insert the probe. Neither of these options is practical.

The embodiment of FIGS. 14A-14B solves this problem by allowing the physician to manually rotate the outer sleeve 415, typically by at least 180° about its longitudinal axis, while holding on to the hand piece and without have to rotate hand piece. As can be seen in FIG. 14A, the outer sleeve 415 is coupled to a rotating core 422 rotatably attached to a distal end or face of the hub 402. A grip tab 426 projects radially from a periphery of the rotating core 422 so that the physician can manually engage the grip tab to rotate the core and the outer sleeve 180° to re-orient the cutting windows and electrode arrangement between an "up" or "down" position. The reorientation of the working end can be done by the physician with one hand, or the physician can hold the handle 405 in one hand and rotate the outer sleeve 415 with the other hand.

In the embodiment shown in FIGS. 14A-14B, the RF source 450 has electrical leads 455a and 455b that extend through the handle 405 and thereafter engage contacts 456a and 456b in the hub 402 that couple to electrical leads extending to the electrode arrangement 420 of the working end. In this arrangement, it should be appreciated that the exterior electrical contacts 456a and 456b in the hub 402 extend to rotating contacts between the hub 402 and the rotating core 422 to thereafter carry electrical current to the active electrode and return electrode of the working end 421.

Figure 15:
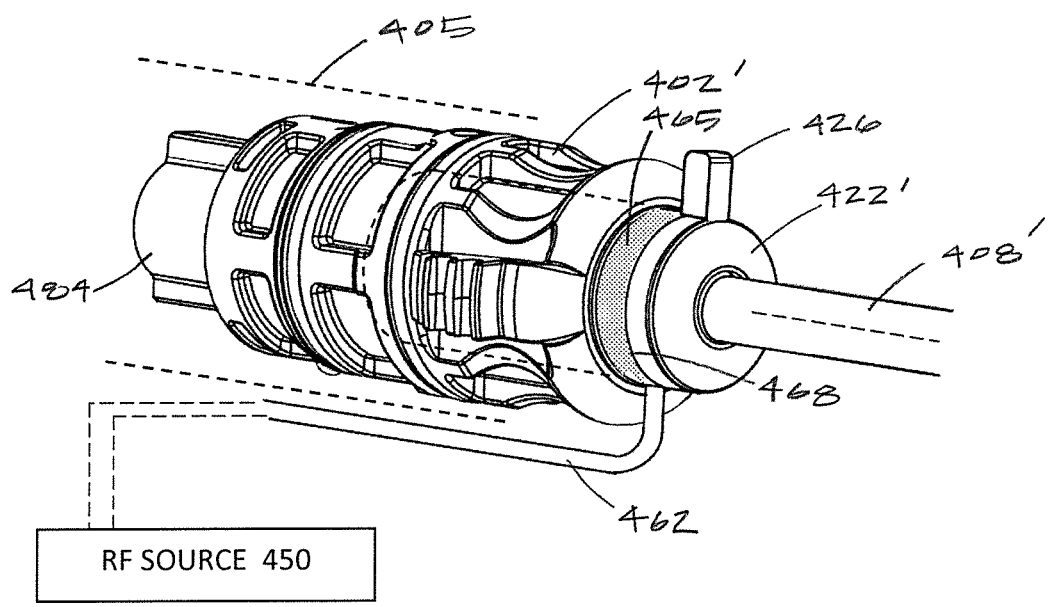
FIG. 15 is a perspective view of a probe variation similar to that of FIGS. 14A-14B except that the electrical connection to the probe is exterior of the handle carrying the motor drive.

FIG. 15 is a perspective view of a probe hub 402' coupled to shaft 408' that extends to a working end similar to that of FIGS. 9-10 or FIGS. 14A-14B except that the electrical connection to the electrode arrangement is carried in a cable 462 at the exterior of the handle 405 which carries the motor drive. In this embodiment, an annular rotatable ring 465 is disposed within an annular notch 468 in the rotating core 422' which has first and second electrical contacts (not shown) coupled to electrical conductors in the shaft 408' that connect to the electrode(s) at the working end of the shaft. It should be appreciated that the electrical cable 462 can be further coupled to a clip in the hub 402 or the hand piece 405 to maintain the cable 462 in a convenient location.

Figure 16:
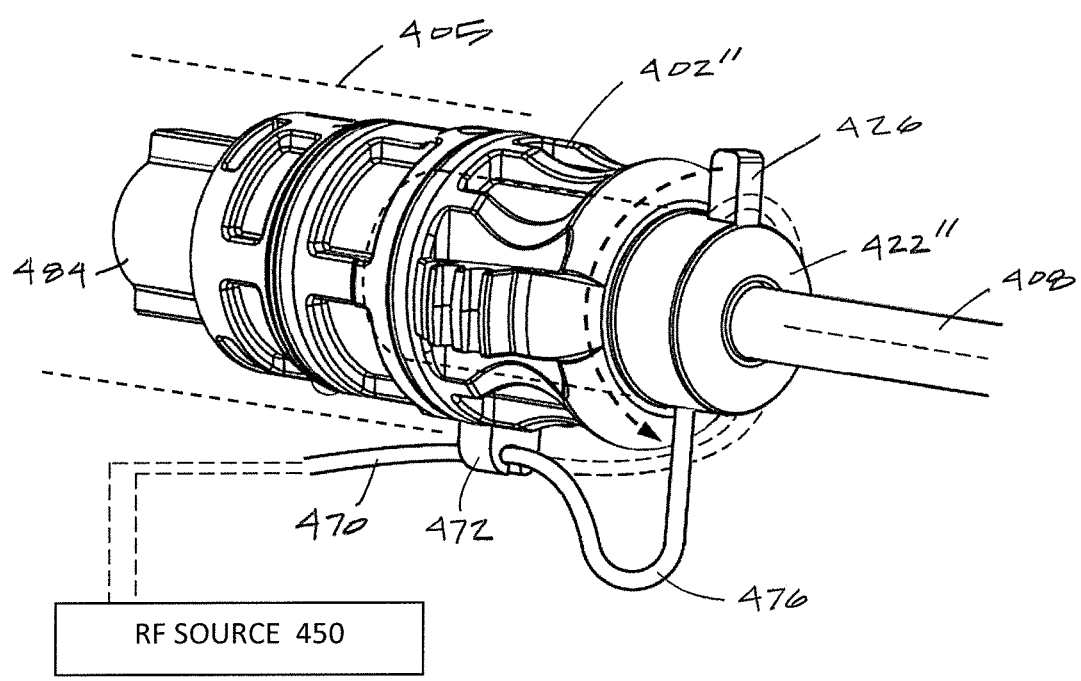
FIG. 16 is a perspective view in another variation other probe similar to that of FIG. 15 with the electrical connection including a slack cable to allow rotation of the shaft relative to the hub.

FIG. 16 is a perspective view of another hub 402" of a probe similar to that of FIG. 15 except that the electrical cable connection to the probe hub differs. In this variation, the cable 470 is held by a clip 472 in the hub 402" to ensure that the cable 470 is not loose to interfere with a physician's manipulations of the device. In this case, the electrical cable 470 has a slack portion 476 between the clip 472 and the rotating core 422" to allow for rotation of the core by 180° or more.

Figure 17:
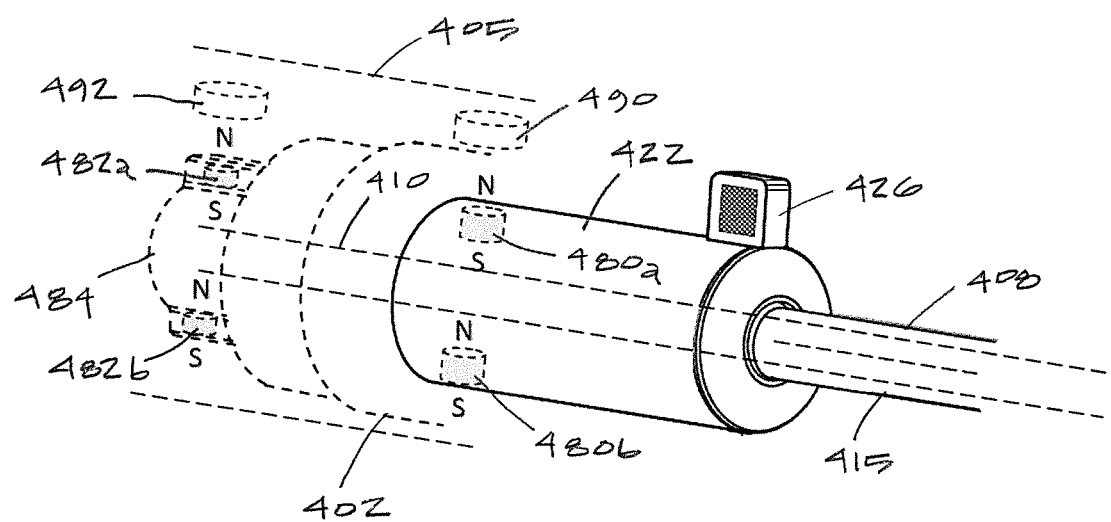
FIG. 17 is a schematic view of the hub of the probe of FIGS. 14A-16 showing magnets carried by components of the hub that allow for the sensor in the hand piece to determine the rotational orientation of both the outer sleeve in the inner sleeve.

FIG. 17 is a schematic view of the rotating core 422 and hub 402 of the probe of FIGS. 14A-14B showing magnets 480a and 480b in the core 422 and magnets 482a and 482b carried by drive coupling 484 that allow for sensors 490 and 492 in the hand piece 405 to determine the rotational orientation of both the outer sleeve 415 and the inner sleeve 410. In other commonly-owned patent applications listed above, systems were described for sensing the rotational position of an inner sleeve relative to an outer sleeve which allows a controller to stop rotation of the inner sleeve cutting window in a window-closed or window-open position. In this embodiment, the same system can be used to stop rotation of the inner sleeve 410 in a selected position to provide such a window-open or window-closed position. However, the manual rotation of the core 422 and outer sleeve 415 means that a controller initially would be required to sense the rotational position of the outer sleeve 415 and its window before determining the desired rotational stop location of the inner sleeve 410. Typically, the outer sleeve 415 will have first and second rotational positions that are 180° apart which indicate the upward or downward orientation of the outer sleeve window and electrode arrangement. In this variation, the controller first senses the orientation of the outer sleeve 415 and then stops rotation of the inner sleeve 410 relative to the outer sleeve window no matter how the outer sleeve 415 is a manually rotated.

FIG. 17 shows the outer sleeve 415 in a typical first position in which the core carries magnets 480a and 480b spaced 180° apart with opposing poles facing outwardly. The hand piece 405 carries sensor 490, such as a Hall sensor, which in adapted to sense the rotational orientation of the core 422 by sensing a magnetic fields of magnets 480a or 480b. Thereafter, the controller can sense the rotational orientation of the drive coupling 484 coupled to the rotatable inner sleeve 410 to determine its movement to a desired rotational stop position. As can be seen in FIG. 17, the drive coupling 484 carries the spaced apart magnets 482a and 482b with opposing poles facing outwardly.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic system, comprising:
   a hand piece with a motor drive; and
   an elongate shaft assembly that includes a hub detachably secured to a distal end of the hand piece, said elongate shaft assembly including an outer sleeve and an inner sleeve rotatably mounted in the outer sleeve, wherein the inner sleeve couples to the motor drive when the elongate shaft assembly is attached to the hand piece and an inner distal cutting window on the inner sleeve moves in and out of alignment with an outer distal cutting window on the outer sleeve as the motor drive rotates the inner sleeve;
   a distal electrode on an outer surface of the outer sleeve at a location opposite to that of the outer distal cutting window;
   wherein the outer sleeve member is rotatable relative to the hand piece when the hub is secured to the hand piece such that a user can hold the hand piece in one hand and rotate the outer sleeve to selectively place the outer distal cutting window or the distal electrode in an upward orientation relative to the user while continuing to hold the hand piece in the one hand.

2. The arthroscopic system of claim 1, wherein the distal electrode comprises an active electrode.

3. The arthroscopic system of claim 2, further comprising a return electrode carried by the shaft assembly.

4. The arthroscopic system of claim 1, wherein the distal electrode and the outer distal cutting window are rotationally spaced-apart by 175° to 195° relative to a longitudinal axis of the shaft.

5. The arthroscopic system of claim 1, further including an actuator coupled to the outer shaft member configured for rotating the outer shaft member between the first and second rotational orientations.

6. The arthroscopic system of claim 5, wherein the actuator comprises a rotating core having a grip tab, wherein the rotating core is rotatably attached to a distal end of the hub.

7. The arthroscopic system of claim 1, further comprising an RF source operatively connected to the electrode.

8. The arthroscopic system of claim 7, wherein the RF source connects to the electrode through electrical contacts in the hand piece that engage cooperating electrical contacts in the hub.

9. The arthroscopic system of claim 8, wherein the RF source connects to the electrode through an electrical cable external to the hand piece.

10. The arthroscopic system of claim 8, wherein the RF source connects to the electrode through an electrical cable coupled to the hub.

11. The arthroscopic system of claim 1, further comprising a first sensor system for sensing the rotational orientation of the outer shaft member relative to the hub when coupled to the hand piece.

12. The arthroscopic system of claim 11, wherein the first sensor system comprises a first sensor carried by the hand piece adapted to sense a magnetic field of at least one magnet carried by the rotatable outer shaft member.

13. The arthroscopic system of claim 12, wherein the first sensor comprises a Hall sensor.

14. The arthroscopic system of claim 12, further comprising a second sensor system for sensing the rotational orientation of the inner shaft member relative to the outer shaft member.

15. The arthroscopic system of claim 14, wherein the second sensor system comprises a second sensor carried by the hand piece adapted to sense a magnetic field of at least one magnet carried by the inner shaft member.

16. The arthroscopic system of claim 15, wherein the second sensor comprises a Hall sensor.

17. The arthroscopic system of claim 15, further comprising a controller operatively coupled to the motor drive, the RF source and the first and second sensor systems, together with a controller algorithm adapted to actuate the motor drive to rotate the inner shaft member to a selected position in response to the outer shaft member being rotated to the first or second rotational orientation.

18. The arthroscopic system of claim 17, wherein the controller algorithm is further adapted to disable the RF source in response to the inner shaft member not being in said selected position.

19. An arthroscopic method performed by a user, comprising:
   providing a probe including a hand piece with a motor drive detachably coupled to a hub of an elongated shaft assembly, the elongated shaft assembly including an outer sleeve with an outer distal cutting window, a distal electrode, and an inner sleeve with an inner distal cutting window;
   introducing a working end of the probe into a treatment space;
   holding the hand piece in the user's hand;
   rotating the outer sleeve about a longitudinal axis of the hand piece while the user holds but does not rotate the hand piece to selectively position either the outer distal cutting window or the distal electrode adjacent to a target tissue site in the treatment space;
   engaging the outer distal cutting window against the targeted tissue and actuating the motor drive to rotate the inner sleeve to resect the target tissue site when the outer distal cutting window is adjacent to the target tissue site; and
   delivering current to the distal electrode when the distal electrode is located adjacent to the target tissue.

20. The arthroscopic method of claim 19, wherein the user manipulates the hand piece without rotating the elongated shaft assembly about the longitudinal axis of the hand piece.

21. The arthroscopic method of claim 19, wherein the user manually rotates the outer sleeve while holding the hand piece.

22. The arthroscopic method of claim 21, wherein the user manually rotates a rotating core rotatably attached to a distal end of the hub and having a grip tab with one hand while holding the hand piece with the other hand.

23. The arthroscopic method of claim 21, wherein the user manually rotates a rotating core rotatably attached to a distal end of the hub and having a grip tab with one hand while holding the hand piece with the same hand.

24. The arthroscopic method of claim 19, further comprising sensing the rotational orientation of the outer shaft member relative to the hand piece with a sensor and controlling the motor drive to rotate the inner shaft member to a selected position relative to the outer shaft member with a controller coupled to the sensor.

25. The arthroscopic method of claim 24, wherein the controller limits energy delivery to the distal electrode when inner shaft member is not in said selected position.

* * * * *